United States Patent
Callendrello et al.

(10) Patent No.: US 9,481,611 B2
(45) Date of Patent: *Nov. 1, 2016

(54) SYSTEM AND METHOD FOR PRODUCING FERTILIZER FROM ORGANIC WASTE

(71) Applicant: NEO Energy, LLC, Portsmouth, NH (US)

(72) Inventors: Anthony M. Callendrello, Exeter, NH (US); Frank W. Getman, Jr., Portsmouth, NH (US); Robert T. Nicholson, Newfields, NH (US)

(73) Assignee: NEO ENERGY, LLC, Portsmouth, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/823,572

(22) Filed: Aug. 11, 2015

(65) Prior Publication Data

US 2015/0368166 A1    Dec. 24, 2015

Related U.S. Application Data

(63) Continuation of application No. 14/087,560, filed on Nov. 22, 2013, now Pat. No. 9,133,068.

(60) Provisional application No. 61/796,975, filed on Nov. 26, 2012.

(51) Int. Cl.
*C05F 17/00* (2006.01)
*C05F 17/02* (2006.01)
(Continued)

(52) U.S. Cl.
CPC ............. *C05F 17/0018* (2013.01); *C05C 1/00* (2013.01); *C05C 9/00* (2013.01); *C05C 11/00* (2013.01); *C05F 17/0027* (2013.01); *C05F 17/0276* (2013.01); *C12M 21/04* (2013.01); *C12M 47/14* (2013.01); *C05F 11/08* (2013.01); *C05F 17/00* (2013.01); *Y02E 50/343* (2013.01);
(Continued)

(58) Field of Classification Search
CPC ....................................................... C05F 17/00
See application file for complete search history.

(56) References Cited

U.S. PATENT DOCUMENTS 3,963,470 A   6/1976  Haug
4,076,515 A   2/1978  Rickard
(Continued)

FOREIGN PATENT DOCUMENTS

CN        1428313         7/2003
DE     102009013880 A1   10/2010
(Continued)

OTHER PUBLICATIONS

International Search Report and Written Opinion dated Jun. 2, 2014, received in PCT/US13/71467.
(Continued)

*Primary Examiner* — Wayne Langel
(74) *Attorney, Agent, or Firm* — McLane Middleton, Professional Association

(57) ABSTRACT

In one aspect, a system for the production of fertilizer from organic waste comprises a microbial digester configured to digest the organic waste, wherein the digestion of the organic waste produces a digestate having a liquids component and a solids component. A spray dryer module is provided for receiving the digestate and reducing moisture content in the digestate to produce a substantially dry fertilizer product. In further aspects, methods and fertilizer compositions are provided.

25 Claims, 2 Drawing Sheets

(51) Int. Cl.
  *C12M 1/107* (2006.01)
  *C12M 1/00* (2006.01)
  *C05C 1/00* (2006.01)
  *C05C 9/00* (2006.01)
  *C05C 11/00* (2006.01)
  *C05F 11/08* (2006.01)

(52) U.S. Cl.
  CPC ............ *Y02P 20/145* (2015.11); *Y02W 30/43* (2015.05); *Y02W 30/47* (2015.05)

(56) References Cited

U.S. PATENT DOCUMENTS

| | | |
|---|---|---|
| 4,137,158 A | 1/1979 | Ishida et al. |
| RE31,185 E | 3/1983 | Greenfield et al. |
| 4,769,149 A | 9/1988 | Nobilet et al. |
| 4,818,405 A | 4/1989 | Vroom et al. |
| 5,417,861 A | 5/1995 | Burnham |
| 6,056,934 A | 5/2000 | Carlsen et al. |
| 6,409,788 B1 | 6/2002 | Sower |
| 6,464,875 B1 | 10/2002 | Woodruff |
| 6,497,741 B2 | 12/2002 | Sower |
| 6,521,129 B1 | 2/2003 | Stamper et al. |
| 6,569,332 B2 | 5/2003 | Ainsworth et al. |
| 6,682,578 B2 | 1/2004 | Sower |
| 6,866,779 B1 | 3/2005 | Burke |
| 7,014,768 B2 | 3/2006 | Li et al. |
| 7,101,481 B2 | 9/2006 | Forrestal et al. |
| 7,135,116 B2 | 11/2006 | Haggerty |
| 7,153,427 B2 | 12/2006 | Burke |
| 7,727,395 B2 | 6/2010 | Fitch et al. |
| 7,811,455 B2 | 10/2010 | Burke |
| 7,927,491 B2 | 4/2011 | Kotelko et al. |
| 8,105,413 B2 | 1/2012 | Burnham |
| 8,221,627 B2 | 7/2012 | Staton et al. |
| 8,287,732 B2 | 10/2012 | Chen et al. |
| 8,329,455 B2 | 12/2012 | Christensen |
| 8,372,274 B2 | 2/2013 | Early et al. |
| 8,492,134 B2 | 7/2013 | Christensen |
| 8,778,135 B2 | 7/2014 | Li et al. |
| 9,133,068 B2 * | 9/2015 | Callendrello ....... C05F 17/0018 |
| 2005/0145566 A1 | 7/2005 | Haase et al. |
| 2006/0086664 A1 | 4/2006 | Wills |
| 2008/0155853 A1 | 7/2008 | Wang et al. |
| 2009/0282882 A1 | 11/2009 | Verhave et al. |
| 2010/0058822 A1 | 3/2010 | Bargiacchi |
| 2010/0071429 A1 | 3/2010 | Von Nordenskjold |
| 2011/0079060 A1 | 4/2011 | Hackett et al. |
| 2011/0154873 A1 | 6/2011 | Burnham et al. |
| 2011/0247378 A1 | 10/2011 | Begley et al. |
| 2012/0174639 A1 | 7/2012 | Herron |
| 2012/0231494 A1 | 9/2012 | Li et al. |
| 2012/0234194 A1 | 9/2012 | Glenn |
| 2012/0247164 A1 | 10/2012 | Dahms et al. |
| 2013/0273629 A1 | 10/2013 | De Jong et al. |
| 2014/0033776 A1 | 2/2014 | Josse et al. |
| 2014/0314657 A1 | 10/2014 | Zhao et al. |
| 2014/0346108 A1 | 11/2014 | Josse et al. |
| 2014/0366596 A1 | 12/2014 | Young et al. |

FOREIGN PATENT DOCUMENTS

| | | |
|---|---|---|
| EP | 427094 A1 | 5/1991 |
| GB | 1513651 | 6/1978 |
| JP | 20032776 | 1/2003 |
| WO | 2014082007 A2 | 5/2014 |

OTHER PUBLICATIONS

European search report dated Jul. 16, 2016, received in European application No. 13856501.5.

* cited by examiner

SYSTEM AND METHOD FOR PRODUCING FERTILIZER FROM ORGANIC WASTE

CROSS REFERENCE TO RELATED APPLICATIONS

This application is a continuation of application Ser. No. 14/087,560 filed Nov. 22, 2013, which claims the priority benefit of U.S. provisional application No. 61/796,975 filed Nov. 26, 2012. Each of the aforementioned applications is incorporated herein by reference in its entirety.

BACKGROUND

The present disclosure relates to methods and systems for producing fertilizer from organic waste and fertilizer compositions prepared by the same. In certain aspects, the present disclosure relates to methods and systems for preparing organic-based fertilizers (e.g., low nitrogen or high nitrogen fertilizers) in dry, water soluble and/or suspendible form, and fertilizer compositions prepared by the same. In some of the presently preferred aspects, the present disclosure relates to methods and systems for preparing high nitrogen content, organic-based fertilizers in dry, water soluble and/or suspendible form, and fertilizer compositions prepared by the same. The fertilizer compositions described herein may advantageously be used for agricultural applications, turf management applications, and others.

Organic waste material, such as food waste, can be converted into useful products or have useful products removed from it. Such methods of processing organic waste include microbic fermentation or digestion, in which microorganisms break down the waste material using biochemical processes.

Anaerobic fermentation involves four distinct stages. The first stage is bacterial hydrolysis in which insoluble molecules such as organic polymers, e.g., carbohydrates, fats, and proteins, are broken down into smaller, water-soluble subunits. The hydrolysis products include simple sugars, lipids, and amino acids that become available for other bacteria.

The second stage is acidogenesis, in which acidogenic bacteria convert the hydrolysis products into volatile fatty acids, which are short chain organic acids, the most important of which is acetic acid, as well as ammonia, hydrogen, and carbon dioxide. The third stage is acetogenesis, in which these bacteria convert the resulting organic acids into acetic acid and additional hydrogen and carbon dioxide. The fourth stage is methanogenesis in which methanogenic microorganisms convert the hydrogen and acetic acid to methane and carbon dioxide.

Commonly, ammonia gas produced by anaerobic fermentation is lost, for example, through volatilization when the anaerobic digestate is removed from the digestion vessel and exposed to atmosphere. Ammonia dissolved in waste water as ammonium ions is also lost in waste water removed from the digestate. The discharge of gaseous ammonia and/or liquid waste water containing ammonium ions can result in environmental and public health concerns. Even in cases where the ammonia is recovered as a waste product, e.g., by ammonia stripping, the loss of nitrogen content from the bio-digestate greatly diminishes its value as a fertilizer. Thus, there exists a need for an organic or organic-based fertilizer having a high nitrogen content. In addition, there exists a need for a fertilizer that can be produced in a substantially dry, water soluble/suspendible form.

Although the present invention is described herein primarily by way of reference to the preferred embodiments wherein the fertilizer product is prepared from an anaerobic digestate, the present system and method is also amenable to the preparation of a substantially dry, water soluble and/or suspendible fertilizer product from a digestate prepared by other types digestion processes, including aerobic digestion of organic materials and anoxic digestion of organic matter.

The present disclosure contemplates a new and improved apparatus, method, and fertilizer product that overcome the above-referenced problems and others.

SUMMARY

In one aspect, a system for the production of fertilizer from organic waste comprises a microbic digester configured to digest the organic waste to produce a digestate having a liquids component and a solids component. A spray dryer module is provided for receiving the digestate and reducing moisture content in the digestate to produce a substantially dry water soluble/suspendible fertilizer product.

In a preferred embodiment, a system for the production of fertilizer from organic waste comprises an anaerobic digester configured to digest the organic waste, wherein the digestion of the organic waste produces a biogas and a digestate having a liquids component and a solids component. A digestate holding tank is in fluid communication with the anaerobic digester for receiving the digestate from the anaerobic digester and in fluid communication with a source of acid for decreasing the pH of the digestate. A solids concentrator, e.g., evaporator, is configured to receive pH-adjusted digestate from the digestate holding tank for removing at least a portion of the liquids component from the pH-adjusted digestate. A spray dryer module is provided for receiving concentrated digestate from the solids concentrator and reducing moisture content from the concentrated digestate to produce a substantially dry fertilizer product.

In a more limited aspect, the microbic digester is selected from an aerobic digester and an anaerobic digester.

In a more limited aspect, the system further comprises a digestate holding tank in fluid communication with the microbic digester for receiving the digestate from the microbic digester and in fluid communication with a source of acid for decreasing the pH of the digestate.

In another more limited aspect, the digestate holding tank is configured to receive the digestate from the microbic digester without exposing the digestate to the atmosphere.

In another more limited aspect, the system further comprises a solids concentration module configured to receive pH-adjusted digestate from the digestate holding tank for removing at least a portion of the liquids component from the pH-adjusted digestate.

In another more limited aspect, the solids concentration module includes an evaporator and a condenser for recovering liquid waste comprising moisture removed from the pH-adjusted digestate.

In another more limited aspect, the system further comprises a filtration module disposed between the digestate holding tank and the solids concentration module, the filtration module comprising one or more filter elements for removing a portion of the solids component.

In another more limited aspect, the filtration module is configured to remove solid particles in the solids component above a preselected threshold size.

In another more limited aspect, the preselected threshold size is in the range of from about 100 microns to about 300 microns.

In another more limited aspect, the system further comprises a solids concentration module coupled to the microbic digester for removing at least a portion of the liquids component from the digestate.

In another more limited aspect, the organic waste is selected from source separated organic waste, food waste, organic byproducts of manufacturing processes, glycerol, glycerin, fats, oils, lipids, grease, yard waste, manure, biosolids, digestible organic materials, and any combination thereof.

In another more limited aspect, the system further comprises a solids collector for collecting the substantially dry fertilizer product.

In another more limited aspect, the microbic digester is an anaerobic digester and the system further comprises a biogas plant coupled to the microbic digester and configured to convert biogas from the microbic digester into one or both of heat and electrical power.

In another more limited aspect, the biogas plant is a combined heat and power (CHP) system.

In another more limited aspect, the system further comprises a purification module coupled to the microbic digester for removing impurities from the biogas.

In another more limited aspect, the purification module includes a scrubber element for removing sulfur containing impurities from the biogas.

In another more limited aspect, the purification module includes a scrubber element for converting one or more sulfur containing compounds in the biogas to sulfuric acid.

In another more limited aspect, the system further comprises an acidulation tank in fluid communication with the purification module and configured to receive the sulfuric acid from the purification module.

In another more limited aspect, the spray dryer module includes one or more high pressure fluid atomization nozzles, two-fluid atomization nozzles, rotary disk atomizers, and/or fluidization beds.

In another more limited aspect, the spray dryer module includes a spray dryer selected from a co-current spray dryer, a counter current spray dryer, and a mixed flow spray dryer.

In another more limited aspect, the system further comprises a vapor collection system including a condenser coupled to the spray dryer module for recovering a condensate comprising moisture removed from the concentrated digestate.

In another aspect, a method for the production of fertilizer, includes obtaining a digestate comprising microbically digested organic waste and having a liquids component and a solids component; and spray drying the digestate to produce a substantially dry fertilizer product.

In a preferred more limited aspect, a method for the production of fertilizer from organic waste includes anaerobically digesting organic waste in an anaerobic digester to produce a biogas and a digestate having a liquids component and a solids component. Ammonia in the digestate is converted to ammonium ion by decreasing the pH of the digestate to produce a pH-adjusted digestate and liquid from the pH-adjusted digestate is evaporated to produce a concentrated digestate having a percentage of solids greater than a percentage of solids of the pH-adjusted digestate. The concentrated digestate is spray dried to produce a substantially dry fertilizer product.

In a more limited aspect, the digestate is selected from aerobically digested organic waste, anaerobically digested organic waste, or a combination thereof.

In more limited aspect, the digestate is obtained by anaerobically digesting the organic waste in an anaerobic digester to produce the digestate and a biogas.

In another more limited aspect, the method further comprises converting ammonia in the digestate to ammonium ion by decreasing the pH of the digestate to produce a pH-adjusted digestate.

In another more limited aspect, the pH of the pH-adjusted digestate is less than 7.0.

In another more limited aspect, the pH of the pH-adjusted digestate is less than 6.0.

In another more limited aspect, the percentage of solids in the pH-adjusted digestate is about 5% by weight and the percentage of solids in the concentrated digestate is in the range of from about 10% to about 20% by weight.

In another more limited aspect, the method further comprises, prior to converting the ammonia to ammonium, transferring the digestate from the anaerobic digester to a holding tank without exposing the digestate to the atmosphere.

In another more limited aspect, the method further comprises evaporating liquid from the digestate to produce a concentrated digestate having a percentage of solids greater than a percentage of solids of the digestate.

In another more limited aspect, the method further comprises removing biogas from the anaerobic digester; and optionally, removing impurities from the biogas.

In another more limited aspect, the method further comprises converting biogas from the anaerobic digester into one or more of heat, electrical power, and pipeline quality gas.

In another more limited aspect, the method further comprises scrubbing the biogas to remove sulfur containing impurities from the biogas.

In another more limited aspect, the scrubbing converts one or more sulfur containing compounds in the biogas to sulfuric acid.

In another more limited aspect, the method further comprises adding at least a portion of the sulfuric acid to the digestate for converting ammonia in the digestate to ammonium ion.

In another more limited aspect, the method further comprises transferring the digestate from the anaerobic digester to a holding tank without exposing the digestate to the atmosphere; converting ammonia in the digestate to ammonium ion by decreasing the pH of the digestate to produce a pH-adjusted digestate; and evaporating liquid from the pH-adjusted digestate to produce a concentrated digestate having a percentage of solids greater than a percentage of solids of the digestate.

In another more limited aspect, the method further comprises condensing moisture removed from the pH-adjusted digestate during the evaporating step to produce a liquid waste; and optionally, delivering at least a portion the liquid waste to one or more of the anaerobic digester, a vessel containing the pH-adjusted digestate, and a waste water treatment facility.

In another more limited aspect, the organic waste is selected from source separated organic waste, food waste, organic byproducts of manufacturing processes, glycerol, glycerin, fats, oils, lipids, grease, yard waste, manure, biosolids, digestible organic materials, and any combination thereof.

In another more limited aspect, the method further comprises, prior to spray drying the digestate, screening the digestate to remove solid particles larger than a preselected threshold size.

In another more limited aspect, the preselected threshold size is in the range of from about 100 microns to about 300 microns.

In another more limited aspect, the method further comprises collecting the substantially dry fertilizer product.

In another more limited aspect, the substantially dry fertilizer product is collected using one or more of a bag filter and cyclonic dust collector.

In another more limited aspect, the method further comprises condensing vapor from the spray drying step to produce a condensate containing moisture removed from the concentrated digestate; and optionally, returning at least a portion of the condensate to the anaerobic digester.

In another more limited aspect, the substantially dry fertilizer product has a nitrogen content of about 10% or greater by weight.

In another more limited aspect, the substantially dry fertilizer product has a moisture content of about 3% to about 4% by weight.

In another more limited aspect, the method further comprises adding one or more additives to the concentrated digestate.

In another more limited aspect, the one or more additives are selected from the group consisting of organic and inorganic forms of nitrogen, soybean meal, soybean flour, cottonseed meal, cottonseed flour, amino acids, lysine, ammonium salts, ammonium sulfate, ammonium nitrate, urea, potassium salts, potassium sulfate, micronutrients, surfactants and combinations thereof.

In another aspect, a fertilizer composition is provided, the fertilizer composition prepared by microbically digesting organic waste to produce a digestate having a liquids component and a solids component and spray drying the digestate to produce a substantially dry fertilizer product.

In a more limited aspect, the fertilizer composition is prepared by anaerobically digesting organic waste in an anaerobic digester to produce a biogas and the digestate.

In another more limited aspect, the fertilizer composition is further prepared by converting ammonia in the digestate to ammonium ion by decreasing a pH of the digestate to produce a pH-adjusted digestate and, prior to spray drying, evaporating liquid from the pH-adjusted digestate to produce a concentrated digestate having a percentage of solids greater than a percentage of solids of the pH-adjusted digestate.

In a preferred, more limited aspect, a fertilizer composition is provided, the fertilizer composition prepared by anaerobically digesting organic waste in an anaerobic digester to produce a biogas and a digestate having a liquids component and a solids component and converting ammonia in the digestate to ammonium ion by decreasing the pH of the digestate to produce a pH-adjusted digestate. Liquid from the pH-adjusted digestate is evaporated to produce a concentrated digestate having a percentage of solids greater than a percentage of solids of the pH-adjusted digestate. The concentrated digestate is spray dried to produce a substantially dry fertilizer product.

One advantage of the present development is that it enables, in certain embodiments, the production of a fertilizer product having high nutrient levels, particularly nitrogen.

Another advantage resides in the product of a fertilizer product being capable of applied through introduction of the fertilizer into irrigation and other water based application systems.

Another advantage of the present development is found in that the fertilizer product can be applied as a solid or admixed with water or other liquid carrier and applied as a liquid. For example, it has been found that the system and method of the present disclosure can be used to produce an organic fertilizer that is highly flowable, thereby allowing for re-suspension in water for spray applications, drip tape applications, application through an irrigation system (fertigation), and so forth.

Still another advantage of the present development is that phytohormones such as auxins and cytokinins in the organic waste are retained in the fertilizer product, thereby significantly enhancing growth and development as well as increasing resistance to environmental stress such as high and low temperature stress, salinity stress, and drought stress.

Yet another advantage of the present development is found in the antioxidants, polyphenols and other bioactive secondary compounds having anti-fungal disease suppressing characteristics that are derived from fruits and vegetables in the organic waste and that are retained in the fertilizer end product.

Still further advantages and benefits of the present invention will become apparent to those of ordinary skill in the art upon reading and understanding the following detailed description of the preferred embodiments.

BRIEF DESCRIPTION OF THE DRAWING

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

The fertilizer compositions in accordance with this disclosure are prepared by the microbial fermentation or digestion of organic waste. Organic waste products which may be used in the presently disclosed process include but are not limited to source separated organic waste, food waste, organic byproducts of manufacturing processes, glycerol, glycerin, fats, oils, lipids, grease, yard waste, manure, biosolids, other digestible organic materials, and any combinations thereof. The present invention will be disclosed primarily by way of reference to the preferred embodiments employing food waste products, e.g., source separated food waste, although the use of other organic waste starting materials is also contemplated.

In preferred embodiments, the organic waste products to be used as feedstock in connection with the digestion process include solid and liquid food waste, including without limitation source separated food waste derived from fruits, vegetables, grains, meats, seafood, liquid dairy, soft drinks, and other associated liquids having nutritional value.

Advantageously, the organic waste feedstock used is of a type containing significant levels of all the basic organic and inorganic nutritional groups including protein, free amino acids, fats/lipids/fatty acids, complex and simple carbohydrates, essential plant inorganic macro-nutrients including nitrogen, phosphorus, potassium, magnesium, calcium, sulfur, and iron which all have beneficial properties that will be conferred to the end product.

The use of food waste as the organic waste feedstock is particularly advantageous since it contains secondary organic and inorganic nutrients that are found at significant levels in food waste and that are typically not found in any other organic waste material. Such secondary nutrients include bioactive compounds such as plant hormones (auxins, cytokinins, gibberellic acid and abscissic acid) and various vitamins from the feedstock, which are also found in the end product fertilizer. Along with these, various fruit and vegetable based antioxidants such as the large group of polyphenols are also found in significant levels within the finished fertilizer product. These secondary bio-active compounds not only impart increased growth and production but also very high levels of naturally induced disease resistance or suppression which results in increased yields. Inorganic essential plant micro-nutrients (zinc, molybdenum, boron, copper, iron and chlorine) are also present in high levels in the food waste and are also preserved in the finished fertilizer product.

Figure 1:
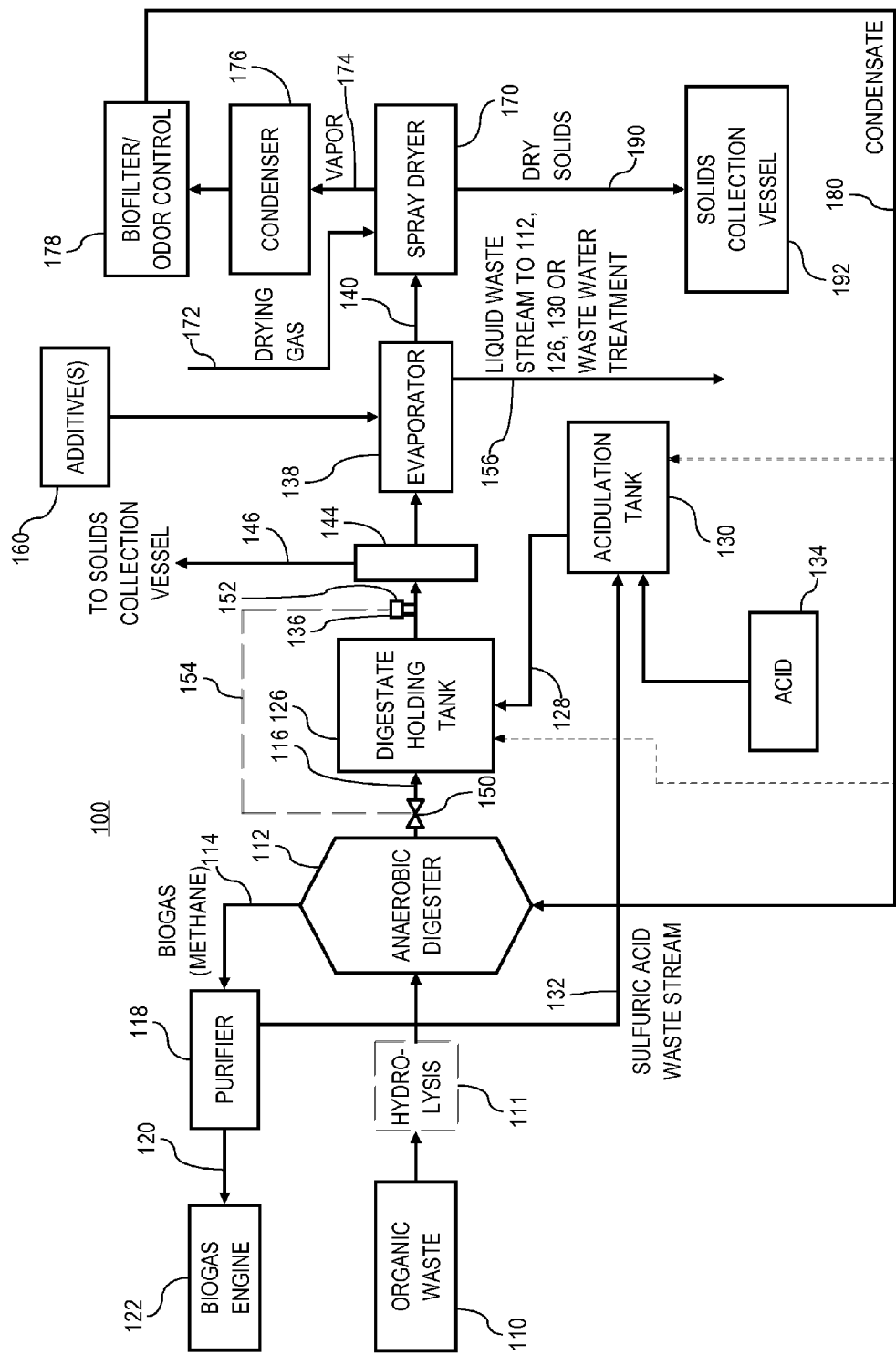
FIG. 1 is a schematic block diagram illustrating an exemplary anaerobic digestion system or apparatus of the present disclosure.
Figure 2:
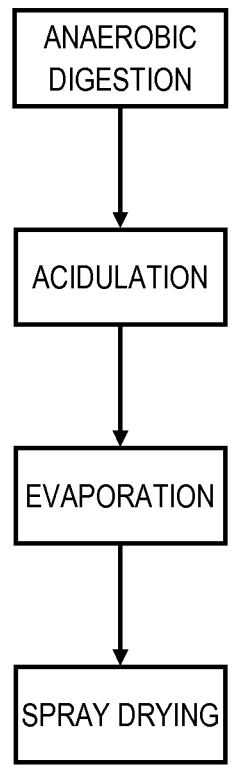
FIG. 2 is a flow chart outlining an exemplary method of the present disclosure.

A preferred embodiment anaerobic digestion system 100 is illustrated in FIG. 1. A flow chart outlining the process appears in FIG. 2, which includes the steps of digestion, acidulation, evaporation/concentration, and spray drying. It will be recognized that the digestion step could be omitted and that the process could start with any source of anaerobic digestate, for example, raw digestate provided by a third party or remotely located digestion facility. Likewise, the acidulation step could be omitted in cases where maximizing nitrogen content in the fertilizer product is not necessary or desired. For example, in some instances it may be desirable to produce a flowable and soluble/suspendible organic fertilizer product which does not use chemical additives such as an acidic chemical reagent during the manufacturing process. In addition, it will be recognized that the evaporation/concentration step could be omitted and that the unconcentrated digestate (whether acidulated or not), could be dried via spray drying.

In the illustrated embodiment, organic waste materials 110, e.g., food waste, are delivered to an anaerobic digester 112, which may be any suitable vat, vessel, or container where anaerobic digestion takes place. The anaerobic digester 112 is generally enclosed to prevent exposure to air and other outside contaminants.

Anaerobic digestion is performed by microorganisms via the hydrolysis, acidogenesis, acetogenesis, and methanogenesis stages, as described above to produce a biogas 114 and a digestate 116. In certain embodiments, the hydrolysis stage of the digestion process can be performed in an optional, separate thermal hydrolysis unit 111. Steam may be utilized to heat the organic waste, and may be provided in part by a service boiler (not shown). To reduce energy consumption and cost, the water may be pre-heated utilizing excess heat from a combined heat and power (CHP) unit 122 cooling jacket and exhaust heat recovery system. Depending on the size of the CHP 122 that is installed, it is possible that all heat requirements could be provided by the CHP 122, leaving the service boiler in standby mode. In alternative embodiments, the hydrolysis unit 111 may be omitted wherein the hydrolysis is performed in the vessel 112.

The anaerobic digestion and subsequent processing of the digestate as described herein can operate continuously or batch mode. The biogas 114 generally contains a mixture of gaseous methane, carbon dioxide, and nitrogen (which can be in the form of ammonia), and others. The biogas 114 also typically contains a quantity of impurities, including sulfides (primarily hydrogen sulfide) among others. The digester 112 may be seeded with anaerobic bacteria as would be understood by persons skilled in the art.

In the illustrated embodiment, the biogas 114 is removed from the digester 112 and is processed by a purifier module 118 as will be discussed in greater detail below. In alternative embodiments the purification module may be omitted. For example, in embodiments, an iron salt such as ferric chloride ($FeCl_3$) is added to the digestion tank to effect removal of hydrogen sulfide during biogas production. The inclusion of an iron salt in the digestion tank also imparts beneficial properties to the fertilizer product.

The biogas may be withdrawn continuously or in batch. Purified biogas 120 may then be delivered to a gas engine 122. In the illustrated preferred embodiment, the gas engine 122 is a combined heat and power (CHP) system. In alternative embodiments, some or all of the purified biogas 120 may be collected and stored for later use. In still other embodiments, the engine 122 can be omitted. For example, in certain embodiments, the biogas is removed from the digester, cleaned if necessary, and stored for later use, injected into a pipeline, etc. The term "biogas" as used herein is intended to encompass further cleaned biogas, e.g., where the biogas is further upgraded to produce natural gas quality methane or so-called biomethane. Since the biogas 122 can be used for many applications in which natural gas would normally be used, the biogas 120 can be used to offset natural gas purchases.

During the digestion process, especially the last stage of methanogenesis, significant levels of ammonia ($NH_3$) are produced from nitrogen containing compounds such as proteins. Since nitrogen is the most important plant fertilizer nutrient, this can be problematic since ammonia is a gas that can and will be lost to the atmosphere via volatilization once the digestate leaves the digester and is exposed to the atmosphere. This is primarily due to the high pH levels generated during the methanogenesis stage of digestion, typically greater than 8.5. The higher the pH, the more ammonia (and, hence, nitrogen) is lost from the system. This volatilization of ammonia is the reason why digestate from conventional anaerobic digesters is low in nitrogen, typically under 1.0% by weight. As such, the huge volumes of liquid digestate from existing anaerobic digestion facilities have very low economic value due both to the low nitrogen and the liquid form. The presently disclosed process and system preserve the nitrogen that would otherwise be lost through ammonia volatilization. The present process is also capable of providing a high or low nitrogen product in a dry, water soluble and/or suspendible form.

The liquid digestate 116 is transferred to a digestate storage tank 126. In the preferred process, the liquid digestate 116 from the digester 112 is not exposed to the atmosphere during transfer, unlike existing anaerobic digestion systems. In certain embodiments, the digestate contains approximately 5% by weight total solids at this point in the process. The digestate 116 is pumped to the holding tank 126 where it is acidulated by adding an acid 128 from an acidulation tank 130. In alternative embodiments, the acidification may occur during the process of transferring the digestate to the tank 126, for example, by adding an acid reagent to a pipe or conduit in which the digestate flows from the digester to the holding tank. As noted above, in other embodiments the acidulation step is omitted.

The acid 128 is preferably sulfuric acid, although it will be recognized that other acids such as phosphoric acid, nitric acid, hydrochloric acid or other acid can also be utilized. The acid 128 is added in a quantity sufficient to bring the pH of the digestate down to within a range in which significant levels of ammonia in the holding tank 126 will be converted into ammonium ($NH_4^+$), which is water soluble. Preferably, the acid 128 is added in a sufficient quantity to bring the pH of the digestate into the acidic range, i.e., under 7.0 and, more preferably, under 6.0. The lower the pH, the more ammonia will be converted to ammonium and retained in the liquid digestate 116. Ammonium is not volatile and will remain in the digestate solution, thereby effectively increasing the nitrogen level going into the first stage of drying within a solids concentration module 138, e.g., an evaporator module.

The anaerobic digestion process produces the biogas 114, which may be used, for example, in the combined heat and power (CHP) generator system 122. Prior to utilization in the engine 122, the biogas 114 requires treatment with the purifier module 118 to remove carbon dioxide, water and other contaminants, primarily hydrogen sulfide ($H_2S$). The purification module 118 includes a scrubber that removes hydrogen sulfide from the biogas as sulfuric acid to produce a highly acidic waste stream 132.

In certain embodiments, the acidic waste stream 132 is delivered to the acidulation tank 130 to be utilized in the digestate acidulation step for pH adjustment of the digestate 116 as described above. This will reduce the quantity of virgin sulfuric acid or other acidic chemical reagent 134 that must be used to achieve a desired pH and reduce the total quantity of waste water 132 from the purifier module 118 sent to the local waste water treatment plant.

After reducing the pH of the digestate 116 to convert ammonia to ammonium, the pH-adjusted digestate 136 is sent, e.g., pumped, to an evaporator or solids concentrator module 138. Reducing the pH of the digestate 116 prior to moving it to the solids concentration module 138 helps retain this level of nitrogen during the evaporation process. Without acidulation of the digestate 116, the evaporation process would result in further lowering the nitrogen content of the liquid digestate due to high pH and higher temperatures, which would both enhance the volatilization and loss of ammonia gas.

In certain embodiments, the evaporation step increases the total solid content of the digestate from about 5% to produce a concentrated digestate 140 having about 10%-20% total solids by weight, and more preferably about 14%-20% total solids by weight. The concentrated digestate 140 is sent to a high-temperature spray dryer module 170 for the next step in the drying process. As noted above, it will be recognized that in certain embodiments the concentration step can be omitted and the process can proceed as otherwise described below but without concentration of the solids in the digestate.

Optionally, prior to entering the evaporation module 138, the pH-adjusted digestate 136 is screened utilizing a filter 144, such as screens, sieves, or other mechanical filtration elements to remove large particles and fibers from the digestate. In preferred embodiments, the filtration media consists of a plurality of screens ranging from about 100 micron to about 300 micron. In a preferred embodiment, the filtration element is a 3-D screen of the type capable of removing elongated fibers or materials from the digestate. Solids/fibers 146 removed from the digestate by the filter 144 may be collected and may be blended with the dry fertilizer product to enhance soil recovery.

In certain embodiments, the solids concentration or evaporation module 138 includes a falling film evaporator and in preferred embodiments employs a multi-stage falling film evaporator coupled with forced circulation evaporation. Flow to the evaporator is controlled via a modulating valve 150 at the digester outlet, based on a signal 154 from a flow meter 152 on the evaporator inlet line. Steam may be utilized to facilitate evaporation and may be provided in part by a service boiler (not shown). To reduce energy consumption and cost, the water may be pre-heated utilizing excess heat from the combined heat and power (CHP) unit 122 cooling jacket and exhaust heat recovery system. Depending on the size of the CHP 122 that is installed, it is possible that all heat requirements could be provided by the CHP 122, leaving the service boiler in standby mode.

Condensate/liquid waste 156 from the evaporator 138 may be returned to the digester 112 and utilized as dilution water for the anaerobic digestion process, and/or to the digestate holding tank 126 and admixed with the digestate 116 to increase the ammonia level prior to evaporation. Excess or unused condensate 156 may be disposed of through the local waste water treatment system.

In certain embodiments, the liquid waste stream 156 generated by the solids concentrator module 138 is condensed and collected in an acidulation tank such as acidulation tank 130, where sulfuric acid or other acidic chemical reagent is added to reduce the pH level and prevent loss of ammonia. The acid used may include sulfuric acid from the optional purifier module 118, if present, virgin sulfuric or other acid, or a combination thereof. In certain embodiments, once the liquid digestate waste 156 is acidulated, e.g., to a pH of less than 6.0, the liquid digestate waste is mixed into the digestate storage tank 126 to increase the concentration of ammonia and assist in reducing the pH of the digestate. In certain embodiments, this process increases the nitrogen level in the digestate from about 0.02% by weight to a range of about 0.8 to about 1.5% by weight.

After the evaporation or concentration step, one or more additives 160 may be added to the concentrated digestate. Such additives may be selected as a supplemental source of nutrients and/or to improve the performance or handling properties of the finished product. The additive or additives 160 are selected to enhance the characteristics of the primary dried powder product 190, depending upon the type of product desired. In certain embodiments, additives may be added in an amount ranging from about 0% to about 30% by weight of the concentrated digestate, and more preferably in the amount of from about 0.5% to about 5% by weight of the concentrated digestate.

Exemplary additives 160 include other organic and inorganic forms of nitrogen such as soybean or cottonseed meals and flours, various amino acids such as lysine, synthetic sources of nitrogen or potassium such as ammonium sulfate, ammonium nitrate, and urea, sulfate of potash (potassium sulfate), micronutrients (e.g., iron, manganese, copper, zinc, molybdenum, boron, chloride, and so forth).

Other additives may include insecticides, fungicides, nematicides, agricultural or horticultural adjuvants, surfactants, and other product enhancing agents which may or may not be organically derived, including without limitation colorants, scents, dispersants, binders, fungicides, mildewcides, or any other additive that would enhance the properties of the dried digestate. It will be recognized that such additives can also be added at other points during the digestion, dehydration, and drying process or directly to the dry fertilizer product.

The concentrated digestate 140 is then delivered to the spray dryer module 170. It has been found that complete drying of the digestate by evaporation and spray drying in accordance with the present disclosure may result in approximately a 10 fold increase in the percentage of nitrogen in the dry product. For example, a 1% nitrogen level in the pH-adjusted digestate 136 by weight will result in a 10% nitrogen content by weight in the dried finished product 200.

Concentrated digestate 140 from the evaporator 138 step has, e.g., approximately 20% total solids when it is pumped to the spray dryer module 170. Any spray dryer may be used in the presently disclosed process. For example, the spray dryer module 170 may employs an atomizer for dispersing the concentrated digestate 140, such as a disk atomizer for spraying the concentrated digestate using a rotating disk or nozzle atomizer. The nozzle atomizer may be, e.g., high pressure single fluid nozzles or two-fluid nozzles using an atomizing gas (e.g., compressed gas).

A heated drying gas is blown in a co-current, counter current, or mixed flow configuration relative to the atomized digestate. In certain embodiments, a fluid bed spray dryer may be employed. In certain embodiments, the drying gas is preheated using the CHP unit 122. In preferred embodiments, the system will operate at temperatures greater than 175 degrees C. and more preferably, at temperatures ranging from about 200 degrees C. to about 300 degrees C.

The spray dryer module 170 reduces the concentrated digestate 140 having about 20% total solids to a substantially dry product. The term "substantially dry product" as used herein is not intended to preclude relatively small amounts of moisture. Preferably, the substantially dry product 190 contains about 1-6% moisture content by weight and more preferably about 3-4% moisture content by weight.

The product 190 is preferably collected as a powder and the spray drying process can be controlled to produce desired particle sizes. In certain embodiments, the dry powder 190 is collected in a solids collection vessel 192, e.g., using a filter bag, a cyclonic dust collector with a filter bag, or the like.

Exhaust gas 174 from the spray dryer 170 is dried using a vapor collection system 176 comprising a condenser. The exhaust gas may also be processed to remove undesirable compounds such volatile organic compounds, malodorous compounds, and so forth. The exhaust gas may be processed, for example, using a biofilter or an ultraviolet/ozone odor control system 178.

Condensate 180 from the condenser 176 may be delivered to the digestion vessel 112 for use as dilution water for the anaerobic digestion process or disposed of via the local waste water treatment system. This results in the return of ammonia lost through vaporization as a result of the relatively high temperatures used during the spray drying process. Alternatively, the condensate 180 may be transferred to the acidulation tank 130 for pH adjustment and use in the digestate holding tank 126 as described above.

During the process in accordance with this disclosure, the ammonium retained in the digestate 116 by acidulation is found in the dried finished fertilizer product 190. Analysis of the material 190 produced from food waste in accordance with this disclosure indicates that, on average 50% of the nitrogen retained in the finished dry product 190 is ammonium (largely ammonium sulfate). This ammonium material is water soluble. The remaining nitrogen in the dry material is low molecular weight organic nitrogen, which is highly suspendible in water. Thus, the resulting form of fertilizer after the spray drying step is a dry powder advantageously containing both the soluble and suspendible fractions of nitrogen. The present system is advantageous in that a water-soluble and/or suspendible powder can be produced having a narrow particle size distribution. In certain exemplary embodiments, the mean particle size of the fertilizer product is in the range of from 5 microns to 5 millimeters, although other particle sizes are contemplated.

In certain embodiments, the powder product 190 can be applied as a dust or powder. Alternatively, the powder product herein can be added back to water and applied to target crops as a slurry or in liquid suspension form, e.g., for spray applications, fertigation or drip irrigation. In still other embodiments, the powder 190 can be used to form pellets or granules for traditional dry fertilizer applications, such as application with drop or rotary spreaders.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A method for the production of fertilizer, comprising the steps of:
   obtaining a raw microbial digestate comprising microbially digested organic waste, the raw microbial digestate being produced from the organic waste by an anaerobic bacterial fermentation process including a hydrolysis stage, an acidogenesis stage, an acetogenesis stage, and a methanogenesis stage, the raw microbial digestate having a liquids component and a solids component;
   acidulating the raw microbial digestate to convert ammonia in the raw microbial digestate to ammonium ion by decreasing a pH of the raw microbial digestate to thereby produce a pH-adjusted digestate; and
   reducing moisture content of the pH-adjusted digestate, said reducing moisture content including spray drying the pH-adjusted digestate to produce a substantially dry fertilizer product.

2. The method of claim 1, wherein the raw microbial digestate is obtained by anaerobically digesting the organic waste in an anaerobic digester using anaerobic bacteria to produce the raw microbial digestate and a biogas.

3. The method of claim 2, further comprising:
   said reducing moisture content further including evaporating moisture from the pH-adjusted digestate to produce a concentrated digestate having a percentage of solids greater than a percentage of solids of the pH-adjusted digestate.

4. The method of claim 2, wherein the pH of the pH-adjusted digestate is less than 7.0.

5. The method of claim 2, wherein the pH of the pH-adjusted digestate is less than 6.0.

6. The method of claim 3, wherein the percentage of solids in the pH-adjusted digestate is about 5% by weight and the percentage of solids in the concentrated digestate is in the range of from about 10% to about 20% by weight.

7. The method of claim 2, further comprising:
   prior to converting the ammonia to ammonium, transferring the raw microbial digestate from the anaerobic digester to a holding tank without exposing the raw microbial digestate to atmosphere.

8. The method of claim 3, wherein the moisture content is reduced using a falling film evaporator.

9. The method of claim 2, further comprising:
removing biogas from the anaerobic digester; and
optionally, removing impurities from the biogas.

10. The method of claim 9, further comprising:
converting biogas from the anaerobic digester into a product selected from the group consisting of heat, electrical power, and pipeline quality gas, and any combination thereof.

11. The method of claim 9, further comprising:
scrubbing the biogas to remove sulfur containing impurities from the biogas.

12. The method of claim 11, wherein the scrubbing converts one or more sulfur containing compounds in the biogas to sulfuric acid.

13. The method of claim 12, further comprising:
adding at least a portion of said sulfuric acid to the raw microbial digestate for converting ammonia in the raw microbial digestate to ammonium ion.

14. The method of claim 2, further comprising:
transferring the raw microbial digestate from the anaerobic digester to a holding tank without exposing the raw microbial digestate to atmosphere; and
evaporating liquid from the pH-adjusted digestate to produce a concentrated digestate having a percentage of solids greater than a percentage of solids of the pH-adjusted digestate.

15. The method of claim 14, further comprising:
condensing moisture removed from the pH-adjusted digestate during the evaporating step to produce a liquid waste; and
optionally, delivering at least a portion the liquid waste to one or more destinations selected from the group consisting of the anaerobic digester, a vessel containing the pH-adjusted digestate, and a waste water treatment facility.

16. The method of claim 1, wherein the organic waste is selected from the group consisting of source separated organic waste, food waste, organic byproducts of manufacturing processes, glycerol, glycerin, fats, oils, lipids, grease, yard waste, manure, biosolids, digestible organic materials, and any combination thereof.

17. The method of claim 1, further comprising one or both of:
prior to spray drying the pH-adjusted digestate, screening the pH-adjusted digestate to remove solid particles larger than a preselected threshold size; and
prior to spray drying the pH-adjusted digestate, evaporating liquid from the pH-adjusted digestate.

18. The method of claim 17, wherein the preselected threshold size is in the range of from about 100 microns to about 300 microns.

19. The method of claim 1, further comprising:
collecting the substantially dry fertilizer product.

20. The method of claim 19, further comprising:
wherein the substantially dry fertilizer product is collected using an apparatus selected from the group consisting of a bag filter, a cyclonic dust collector, and a combination thereof.

21. The method of claim 1, further comprising:
condensing vapor from the spray drying step to produce a condensate containing moisture removed from the concentrated digestate; and
optionally, returning at least a portion of the condensate to a digestion vessel.

22. The method of claim 1, wherein the substantially dry fertilizer product has a nitrogen content of about 10% or greater by weight.

23. The method of claim 1, wherein the substantially dry fertilizer product has a moisture content of about 3% to about 4% by weight.

24. The method of claim 1, further comprising:
adding one or more additives to the concentrated digestate.

25. The method of claim 24, wherein the one or more additives are selected from the group consisting of organic and inorganic forms of nitrogen, soybean meal, soybean flour, cottonseed meal, cottonseed flour, amino acids, lysine, ammonium salts, ammonium sulfate, ammonium nitrate, urea, potassium salts, potassium sulfate, micronutrients, surfactants and combinations thereof.

* * * * *